(12) United States Patent
Towart et al.

(10) Patent No.: US 6,258,828 B1
(45) Date of Patent: Jul. 10, 2001

(54) CHELATING AGENTS AND THEIR METAL CHELATES FOR TREATING FREE RADICAL INDUCED CONDITIONS

(75) Inventors: Robertson Towart, Stoke Poges (GB); Jan O. G. Karlsson, Nesoddtangen; Per Jynge, Trondheim, both of (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/213,290

(22) Filed: Dec. 17, 1998

Related U.S. Application Data (63) Continuation of application No. PCT/GB97/01722, filed on Jun. 24, 1996.

(30) Foreign Application Priority Data

Jun. 24, 1996 (GB) .................................. 9613182

(51) Int. Cl.⁷ .................. A61K 31/44; C07D 213/62
(52) U.S. Cl. .................................. 514/335; 546/261
(58) Field of Search ............... 546/261; 514/335

(56) References Cited

U.S. PATENT DOCUMENTS

| | | | |
|---|---|---|---|
| 4,842,845 | * | 6/1989 | Rocklage et al. ............. 424/1.77 |
| 4,935,518 | * | 6/1990 | Rocklage et al. ............. 546/6 |
| 5,223,243 | * | 6/1993 | Rocklage et al. ............. 424/9.361 |

FOREIGN PATENT DOCUMENTS

WO94 15925 A1  7/1994 (WO).

OTHER PUBLICATIONS

Rocklage, et. al., Structural and Thermodynamic Characterization of Manganese (II) N,N′-Dipyridoxylethylenediamine- N,N′-diacetate. A Novel Manganese (II) Chelate, Inorg. Chem., vol. 27, pp. 3530–3534, 1988.*
Bowers–Komro, et. al., Single– and Double–Headed Analogs of Pyridoxamine 5′-Phosphate as Probes for Pyridoxamine 5′-Phosphate Utilizing Enzymes, Bioorganic Chemistry vol. 15, pp. 224–236, 1987.*
Asplund et al., J. Pharmacol. Exp. Ther., 271(2): 609–614 (1994).
Brurok et al., Invest. Radiol., 30(3):159–167 (1995).
Parat et al., Free Rad. Res., 23(4): 339–351 (1994).
Sorenson; Radiat. Res., 132(1):19–29 (1992).
Brurok et al., Invest. Radiol., 32(4): 205–211 (1997).
Saeed et al., Radiology, 172(1):59–64 (1989).
Misselwitz et al., Invest. Radiol., 30(10): 611–620 (1995).
Proctor et al., Physiol. Chem. Physics Med. NMR, 6(3): 175–195 (1984).

* cited by examiner

*Primary Examiner*—Zinna Northington Davis
*Assistant Examiner*—Binta Robinson
(74) *Attorney, Agent, or Firm*—Bacon & Thomas

(57) ABSTRACT

The invention provides the use of a compound of formula (I) or a metal chelate or salt thereof in the manufacture of a therapeutic agent for use in the treatment of prophylaxis of conditions resulting from the presence of free radicals in the human or non-human animal body (wherein in formula (I): each $R^1$ independently represents hydrogen or $-CH_2COR^5$; $R^5$ represents hydroxy, optionally hydroxylated alkoxy, amino or alkylamido; each $R^2$ independently represents a group $XYR^6$; X represents a bond, or a $C_{1-3}$ alkylene or oxoalkylene group optionally substituted by a group $R^7$; Y represents a bond, an oxygen atom or a group $NR^6$; $R^6$ is a hydrogen atom, a group $COOR^8$, an alkyl, alkenyl, cycloalkyl, aryl or aralkyl group optionally substituted by one or more groups selected from $COOR^8$, $CONR^8{}_2$, $NR^8{}_2$, $OR^8$, $=NR^8$, $=O$, $OP(O)(OR^8)R^7$ and $OSO_3M$; $R^7$ is hydroxy, an optionally hydroxylated, optionally alkoxylated alkyl or aminoalkyl group; $R^8$ is a hydrogen atom or an optionally hydroxylated, optionally alkoxylated alkyl group; M is a hydrogen atom or one equivalent of a physiologically tolerable cation; $R^3$ represents a $C_{1-8}$ alkylene group, a 1,2-cycloalkylene group, or a 1,2-arylene group; and each $R^4$ independently represents hydrogen or $C_{1-3}$ alkyl). Such compounds are particularly effective in relieving symptoms associated with reperfusion of ischemic tissue and in treating or preventing radiation-induced injury.

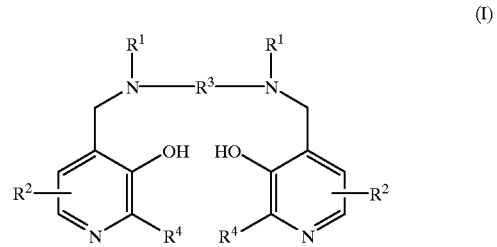

(I)

17 Claims, 4 Drawing Sheets

normally perfused area
area at risk (non perfused during occlusion)
infarction
ventricles

FIG. 4.

CHELATING AGENTS AND THEIR METAL CHELATES FOR TREATING FREE RADICAL INDUCED CONDITIONS

This application is a continuation application of pending international application number PCT/GB97/01722 filed Jun. 24, 1996, of which entire disclosure of the pending, prior application is hereby incorporated by reference.

The present invention relates to the use of chelating agents and their metal chelates in medicine, in particular in treating conditions resulting from the presence of free radicals in the body, e.g. in the treatment of ischaemia-related diseases.

Short-lived but highly reactive free radicals have long been believed to be involved in various sorts of tissue damage, especially during reperfusion of ischaemic tissue and in radiation-induced injury. A key factor in the production of many free radicals is believed to be the availability of ferric ions which stimulate the formation of free radicals, such as hydroxyl, peroxyl and hydroperoxyl radicals, and singlet oxygen which cause membrane damage via lipid peroxidation.

Ischaemia-related diseases, in particular coronary artery diseases, account for the majority of deaths in Western countries. The reintroduction of oxygenated blood into ischaemic tissues can, in many cases, result in various forms of cardiac dysfunction, including arrhythmias, myocardial "stunning", arterial spasm and endothelial damage (Kirschner et al. J. Amer. College of Surgeons 179: 103–117 (1994)). Furthermore, inactivation of NO, believed to have cardioprotective effects, can occur (see e.g. Vegh et al. Br. J. Pharmacol. 107: 910–911 (1992) and Lefer et al. Circulation 88: 2337–2350 (1993)).

Recent studies suggest that reperfusion injuries are largely a result of the production of oxygen-derived free radicals during reoxygenation of the perfused tissues. This is particularly so not only during the introduction of blood and oxygen during the early reperfusion period, but also in the subsequent protracted period of inflammatory response in the previously ischemic tissues.

It will be appreciated that there thus exists a continuing need for compounds which are able to treat or prevent conditions arising from the presence of free radicals in the body, in particular compounds which are able to prevent reperfusion injuries.

The medical use of chelating agents and their metal chelates is well established, for example in diagnostic techniques such as X-ray, magnetic resonance imaging (MRI), ultrasound imaging or scintigraphy. A wide variety of chelating agents and metal chelates are known or have been described.

Aminopoly (carboxylic acid or carboxylic acid derivative) chelating agents and their metal chelates are well known and are described for example in EP-A-299795, EP-A-71564, DE-A-3401052, EP-A-203962 and EP-A-436579.

Dipyridoxyl based chelating agents and their chelates with trivalent metals have been described by Taliaferro (Inorg. Chem. 23: 1183–1192 (1984)). The compound N,N'-dipyridoxyl ethylenediamine-N,N'-diacetic acid (PLED) has been evaluated as a chelating agent for the preparation of gallium or indium containing radiopharmaceuticals (see Green et al. Int J. Nucl. Med. Biol, 12(5): 381–386 (1985)).

A number of PLED derivatives and analogues have also been described for use in MRI contrast media, in particular the chelating agent N,N'-bis-(pyridoxal-5-phosphate)-ethylenediamine-N,N'-diacetic acid (DPDP) and its manganese (II) chelate, Mn DPDP (see EP-A-290047 and EP-A-292761).

We have now found that certain chelating agents, in particular dipyridoxyl and aminopolycarboxylic acid based chelating agents, and their metal chelates are particularly effective in treating or preventing tissue damage caused by free radicals and which are capable of relieving symptoms associated with reperfusion of ischaemic tissue.

In one aspect the invention provides the use of a compound of formula I (I)

or a metal chelate or salt thereof in the manufacture of a therapeutic agent for use in the treatment or prophylaxis of conditions resulting from the presence of free radicals in the human or non-human animal body (wherein in formula I each $R^1$ independently represents hydrogen or —$CH_2COR^5$;

$R^5$ represents hydroxy, optionally hydroxylated alkoxy, amino or alkylamido;

each $R^2$ independently represents a group $XYR^6$;

X represents a bond, or a $C_{1-3}$ alkylene or oxoalkylene group optionally substituted by a group $R^7$;

Y represents a bond, an oxygen atom or a group $NR^6$;

$R^6$ is a hydrogen atom, a group $COOR^8$, an alkyl, alkenyl, cycloalkyl, aryl or aralkyl group optionally substituted by one or more groups selected from $COOR^8$, $CONR^8{}_2$, $NR^8{}_2$, $OR^8$, =$NR^8$, =O, OP(O) $(OR^8)R^7$ and $OSO_3M$;

$R^7$ is hydroxy, an optionally hydroxylated, optionally alkoxylated alkyl or aminoalkyl group;

$R^8$ is a hydrogen atom or an optionally hydroxylated, optionally alkoxylated alkyl group;

M is a hydrogen atom or one equivalent of a physiologically tolerable cation, e.g. an alkali or alkaline earth cation, an ammonium ion or an organic amine cation, such as a meglumine ion;

$R^3$ represents a $C_{1-8}$ alkylene group, preferably a $C_{1-6}$, e.g. a $C_{2-4}$ alkylene group, a 1,2-cycloalkylene group, or a 1,2-arylene group; and each $R^4$ independently represents hydrogen or $C_{1-3}$ alkyl).

In another aspect the invention provides a method of treatment of the human or non-human animal body to combat or prevent conditions associated with the presence of free radicals in the body, said method comprising administering to said body a compound of formula I or a metal chelate or salt thereof.

Other chelators suitable for use in the method of the invention include the macrocyclic and more preferably linear or branched aminopolycarboxylic acid chelants of EP-A-299795, EP-A-71564, DE-A-3401052, EP-A-203962, EP-A-436579 and the phosphorus oxyacid analogs. Preferred chelating agents include amides of DTPA and EDTA in which the nitrogens of the amide groups may be substituted by one or more $C_{1-18}$ alkyl groups, e.g. DTPA.BMA and EDTA.BMA.

As used herein the terms "alkyl" and "alkylene" include both straight-chained and branched, saturated and unsaturated hydrocarbons. The term "1,2-cycloalkylene" includes both cis and trans cycloalkylene groups and alkyl substituted cycloalkylene groups having from 5–8 carbon atoms. The term "1,2-arylene" includes phenyl and napthyl groups and alkyl substituted derivatives thereof having from 6 to 10 carbon atoms.

Unless otherwise specified, any alkyl, alkylene or alkenyl moiety may conveniently contain from 1 to 20, preferably 1–8, more preferably 1–6 and especially preferably 1–4 carbon atoms.

Cycloalkyl, aryl and aralkyl moieties may conveniently contain 3–18, preferably 5–12 and especially preferably 5–8 ring atoms. Aryl moieties comprising phenyl or naphthyl groups are preferred. As aralkyl groups, phenyl $C_{1-3}$ alkyl, especially benzyl, are preferred.

Where groups may optionally be substituted by hydroxy groups, this may be monosubstitution or polysubstitution and, in the case of polysubstitution, alkoxy and/or hydroxy substituents may be carried by alkoxy substituents.

In formula I, $R^5$ is preferably hydroxy, $C_{1-8}$ alkoxy, ethylene glycol, glycerol, amino or $C_{1-8}$ alkylamido. Preferably each group $R^1$ represents —$CH_2COR^5$ in which $R^5$ is hydroxy.

In the compounds of formula I, X is preferably a bond or a group selected from $CH_2$, $(CH_2)_2$, CO, $CH_2CO$, $CH_2CH_2CO$ or $CH_2COCH_2$. Preferably, Y represents a bond.

The compounds of formula I may have the same or different $R^2$ groups on the two pyridyl rings and these may be attached at the same or different ring positions. However, it is especially preferred that substitution be at the 5- and 6-positions, most especially the 6-position, i.e. para to the hydroxy group. Compounds in which the $R^2$ groups are identical and identically located, e.g. 6,6', are especially preferred.

Preferred as groups $R^6$ are mono- or poly(hydroxy or alkoxylated) alkyl groups or a group of the formula $OP(O)(OR^8)R^7$.

$R^7$ is preferably hydroxy or an unsubstituted alkyl or aminoalkyl group.

Particularly preferred identities for group $R^2$ include $CHR^7OCO(CH_2)_xPh$ and $CHR^7OCO(CH_2CO)_xPh$ (wherein x is 1 to 3), $CHR^7OCOBu^t$, $CH_2N(H)R^{6'}$, $CH_2N(R^{6'})_2$, $N(H)R^{6'}$, $N(R^{6'})_2$, $CH_2OH$, $CH_2OR^{6'}$, $COOR^{6'}$, $CON(H)R^{6'}$, $CON(R^{6'})_2$ or $OR^{6'}$ (where $R^{6'}$ is a mono- or polyhydroxylated, preferably $C_{1-4}$, especially preferably $C_{1-3}$, alkyl group), $(CH_2)_nCOOR^{7'}$ (wherein n is 1 to 6), $COOR^{7'}$ (where $R^{7'}$ is a $C_{1-4}$ alkyl, preferably $C_{1-3}$, especially preferably a methyl group), $CH_2OSO_3^-M$, $CH_2CH_2COOH$, $CH_2OP(O)(OH)(CH_2)_3NH_2$, $CH_2OP(O)(OH)CH_3$ or $CH_2OP(O)(OH)_2$ group). Yet more preferably, $R^2$ represents a group of the formula $CH_2OP(O)(OH)_2$.

Compounds of formula I in which $R^3$ is ethylene and $R^2$ has any of the identities listed above are particularly preferred.

Preferred metal chelates of the compounds for use in the method of the invention are those in which the metal ions are selected from the alkali and alkaline earth metals and from those metals having an atomic number from 22–31, 42, 44 and 58–70 and more particularly chelates having a $K_a$ in the range from $10^9$ to $10^{25}$, preferably $10^{10}$ to $10^{24}$, more preferably $10^{11}$ to $10^{23}$, e.g. $10^{12}$ to $10^{22}$. Particularly preferred chelates are those with metals other than iron which have a $K_a$ value smaller, preferably by a factor of at least $10^3$, than the $K_a$ value of the corresponding iron ($Fe^{3+}$) chelate. Suitable ions include $Na^+$, $Mn^{2+}$, $Ca^{2+}$, $Zn^{2+}$, $Cu^{2+}$, $Cu^+$, $Gd^{3+}$ and $Mg^{2+}$. $Mn^{2+}$ is especially preferred.

As chelates of aminopolycarboxylic acids, Mn DTPA.BMA and Mn EDTA.BMA are particularly preferred for use in accordance with the invention.

More particularly, preferred for use in accordance with the invention is the compound N,N'-bis-(pyridoxal-5-phosphate)-ethylenediamine-N,N'-diacetic acid or N,N'-bis(3-hydroxy-2-methyl-5-phosphonomethyl-4-pyridyl-methyl)-ethylenediamine-N,N'-diacetic acid (hereinafter referred to as DPDP) and the manganese (II) chelate, Mn(DPDP).

If not all of the labile hydrogens of the chelates are substituted by the complexed metal ion, biotolerability and/or solubility of the chelate may be increased by substituting the remaining labile hydrogen atoms with physiologically biocompatible cations of inorganic and/or organic bases or amino acids. Examples of suitable inorganic cations include $Li^+$, $K^+$, $Na^+$ and especially $Ca^{2+}$. Suitable organic cations include ammonium, substituted ammonium, ethanolamine, diethanolamine, morpholine, glucamine, N,N,-dimethyl glucamine, lysine, arginine or ornithine.

The chelating agents and the metal chelates thereof for use in accordance with the invention are particularly effective in the treatment or prevention of reperfusion-induced injuries, such as arrhythmias and endothelial damage which may occur during thrombolytic treatment, after reperfusion in cardio-pulmonary bypass, percutaneous transluminal coronary angioplasty (PTCA), and in cardiac surgery, including cardiac transplantation. A preferred use of the compounds herein described is in reducing myocardial reperfusion injury, e.g. following myocardial infarction arising from severe or acute myocardial ischemia.

A further use of the compounds of the invention is in relation to organ transplantation, e.g. with cardiac, liver, kidney or brain transplants. In this regard, the compounds may be administered to the organ donor or recipient either prior to, during or subsequent to transplant surgery. A preferred use of the compounds is as an organ transplant solution in which organs may be stored prior to transplantation.

The compounds for use in accordance with the invention are also effective in treating or preventing pro-inflammatory disorders, particularly in treating or preventing radiation-induced injury, e.g. in radiotherapy.

The chelating agents and metal chelates for use in the method of the invention are effective if administered following reperfusion of ischemic tissue. However, such compounds are also effective to prevent reperfusion-induced injury, e.g. following myocardial ischemia, if administered after the onset of interruption in coronary blood flow but prior to the onset of reperfusion. As a result, the method of the invention is applicable not only to cases where myocardial ischemia is expected, e.g. during cardio-pulmonary bypass, PTCA and in cardiac surgery, but also in cases where myocardial ischemia is not planned, e.g. during cardiac arrest and during thrombolysis. In this regard, the compounds herein described are particularly useful as an adjunct to thrombolysis.

Viewed from a further aspect the invention thus provides a pharmaceutical composition comprising a chelating agent according to the invention or a metal chelate or salt thereof, together with one or more thrombolytic agents, and at least one pharmaceutically acceptable carrier or excipient.

Viewed from a yet still further aspect the invention provides a pack containing a chelating agent according to the invention or a metal chelate or salt thereof and separately a thrombolytic agent for simultaneous, separate or sequential use during a thrombolytic procedure.

In another aspect the invention provides the use of a chelating agent according to the invention or a metal chelate or salt thereof together with one or more thrombolytic agents in the manufacture of a medicament for use during a thrombolytic procedure.

The invention further provides a method of treatment of a human or non-human animal body, said method comprising administering to said body an effective amount of a compound of formula I or a metal chelate or salt thereof, and a throboytic agent, simultaneously, separately or sequentially during a thrombolytic procedure.

Examples of thrombolytic agents suitable for use in accordance with the invention include aspirin, plasmin, prourokinase, streptokinase, tissue plasminogen activator, urokinase, hirudin and anti-platelet drugs.

The compounds of the invention may be prepared by methods known in the art. Suitable methods for preparing the amino polycarboxylic acid based chelating agents are described in EP-A-299795, EP-A-71564, DE-A-3401052, EP-A-203962 and EP-A-436579.

In preparing the dipyridoxyl compounds, the compound PLED may be used as a starting material and may be appropriately derivatised using conventional procedures to obtain the compounds of formula I.

Suitable methods for preparing the compounds of formula I are described for example in EP-A-290047.

Alternatively the compounds of formula I may be prepared by reacting the corresponding pyridoxal compound with an alkylene diamine according to the procedure for making PLED described by Taliaferro (supra).

Alternatively, the compounds in accordance with the invention may be prepared by a process comprising one or more of the following steps:

(a) reacting a compound of formula II with a diamine of formula (III)

(wherein $R^3$ and $R^4$ are as hereinbefore defined and $R^{2'}$ is an optionally protected group $R^2$ as hereinbefore defined)

(b) hydrogenating a compound of formula (IV) obtained in step (a)

(wherein $R^3$, $R^4$ and $R^{2'}$ are as hereinbefore defined)

(c) reacting a compound of formula (V)

(wherein $R^3$, $R^4$ and $R^{2'}$ are as hereinbefore defined) with a haloacetic, preferably bromoacetic, acid, and if necessary removing any protecting groups used; and (d) converting a compound of formula I into a chelate complex or salt thereof.

Pyridoxyl phosphate, pyridoxal and the other compounds of formula II and the alkylene diamine, cycloalkylene diamine and arylene compounds of formula III are well-known compounds readily available or can be readily synthesised by procedures well known in the art.

The reaction of step (a) may conveniently be performed in a suitable solvent, such as an alcohol (e.g. methanol) at a temperature in the range of from 0 to 60° C.

To obtain compounds of formula I where the $R^2$ groups are the same, a diamine of formula III may be reacted with two molar equivalents of a compound of formula II. For the preparation of compounds of formula I where the $R^2$ groups are different, the diamine of formula III is first reacted with a first compound of a formula II having a desired $R^{2'}$ group, and the reaction product thereby obtained is then reacted with a second compound of formula II bearing a different $R^{2'}$ group.

The hydrogenation of step (b) may be performed using conventional procedures, e.g. using a palladium or platinum calalyst.

The metal chelates for use in accordance with the invention may be formed by conventional procedures known in the art. In general, such processes involve disssolving or suspending a metal oxide or metal salt (e.g. nitrate, chloride or sulfate) in water or a lower alcohol such as methanol, ethanol, or isopropanol. To this solution or suspension is added an equimolar amount of the chelating agent in water or a lower alcohol and the mixture is stirred, if necessary with heating moderately or to the boiling point, until the reaction is completed. If the chelate salt formed is insoluble in the solvent used, the reaction product is isolated by filtering. If it is soluble, the reaction product is isolated by evaporating to dryness, e.g. by spray drying or lyophilising.

If acid groups such as the phosphoric acid groups are still present in the resulting chelate, it is advantageous to convert the acidic chelate salt into a neutral chelate salt by reaction with inorganic and/or organic bases or amino acids, which form physiologically acceptable cations, and to isolate them.

The carboxylic and phosphoric acid groups of the chelating agents can also be neutralised by esterification to prepare carboxylate and phosphate esters. Such esters can be prepared from the corresponding alcohols by conventional procedures known in the art. Suitable esters include, for example, esters of straight-chained or branched alcohols having from 1 to 18 carbon atoms, mono and polyhydric alkyl amino alcohols having from 1 to 18 carbon atoms, preferably having from 1 to 6 carbons, such as serinol or diethanolamine, and polyhydric alcohols having from 1 to 18 carbon atoms, such as ethylene glycol or glycerol.

Where the metal chelate carries an overall charge it will conveniently be used in the form of a salt with a physiologically acceptable counterion, for example an ammonium, substituted ammonium, alkali metal or alkaline earth metal (e.g. calcium) cation or an anion deriving from an inorganic or organic acid. In this regard, meglumine salts are particularly preferred.

The therapeutic agents of the present invention may be formulated with conventional pharmaceutical or veterinary formulation aids, for example stabilizers, antioxidants, osmolality adjusting agents, buffers, pH adjusting agents, etc. and may be in a form suitable for parenteral or enteral administration, for example injection or infusion or administration directly into a body cavity having an external escape duct, for example the gastrointestinal tract, the bladder or the uterus. Thus the agent of the present invention may be in a conventional pharmaceutical administration form such as a tablet, capsule, powder, solution, suspension, dispersion, syrup, suppository, etc. However, solutions, suspensions and dispersions in physiologically acceptable carrier media, for example water for injections, will generally be preferred.

The compounds according to the invention may therefore be formulated for administration using physiologically acceptable carriers or excipients in a manner well-known to those skilled in the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (e.g. tromethamine hydrochloride), additions (e.g. 0.01 to 10 mole percent) of chelants (such as, for example, DTPA, DTPA-bisamide or non-complexed chelants of formula I) or calcium chelate complexes (e.g. calcium DTPA, CaNaDTPA-bisamide, calcium salts or chelates of chelants of formula I), or, optionally, additions (e.g. 1 to 50 mole percent) of calcium or sodium salts (e.g. calcium chloride, calcium ascorbate, calcium gluconate or calcium lactate combined with metal chelate complexes of chelating agents according to the invention and the like).

If the compounds are to be formulated in suspension form, e.g., in water or physiological saline for oral administration, a small amount of soluble chelate may be mixed with one or more of the inactive ingredients traditionally present in oral solutions and/or surfactants and/or aromatics for flavouring.

The preferred mode for administering the metal chelates in accordance with the invention is parenteral, e.g. intravenous or intra-arterial administration. Parenterally administrable forms, e.g. intravenous solutions, should be sterile and free from physiologically unacceptable agents, and should have low osmolality to minimize irritation or other adverse effects upon administration, and thus the compositions should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions may contain preservatives, antimicrobial agents, buffers and antioxidants conventionally used for parenteral solutions, excipients and other additives which are compatible with the chelates and which will not interfere with the manufacture, storage or use of the products.

The therapeutic agent in accordance with the invention, if in solution, suspension or dispersion form, will generally contain the chelant or metal chelate at a concentration in the range of from 0.0001 to 5.0 moles per liter, preferably 0.01 to 0.1 moles per liter. If convenient, the therapeutic agent may however be supplied in a more concentrated form for dilution prior to administration.

The therapeutic agent in accordance with the invention may conveniently be administered in amounts of from $10^{-2}$ to 100 $\mu$mol of the compounds per kilogram of body weight, e.g. about 10 $\mu$mol per kg bodyweight.

BRIEF DESCRIPTION OF DRAWING

The present invention will now be illustrated further by the following non-limiting Examples and with reference to the attached figures, in which.

EXAMPLE 1

The protective effect of MnDPDP against myocardial injury during hypoxia and reoxygenation was demonstrated ex vivo.

Method

Isolated rat hearts were perfused in the Langendorff mode at a constant flow rate (10 ml/min) at 37° C. The perfusion medium (glucose-containing Krebs Henseleit's bicarbonate buffer) was equilibrated with 95% $O_2$+5% $CO_2$ during normoxic conditions and with 95% $N_2$+5% $CO_2$ during hypoxia. Left ventricular (LV) developed pressure (LVDP), a main indicator of contractile function, was measured using a fluid-filled LV balloon connected to a pressure transducer and recording system. The coronary effluent was collected at intervals for the measurement of myocardial lactate dehydrogenase (LDH) release by a standard enzymatic technique.

The experimental time course (170 min) involved: control period 0–20 minutes (20 min normoxic perfusion); hypoxic period 20–140 minutes (120 min hypoxic perfusion); and reoxygenation period 140–170 minutes (30 min normoxic perfusion). Two experimental groups were studied: (a) MnDPDP group (n=3) with MNDPDP 30 $\mu$M present in the perfusate during the entire hypoxic period plus during the initial 10 minutes of reoxygenation; and (b) a non-treated control group (n=3).

Results

Figure 1:
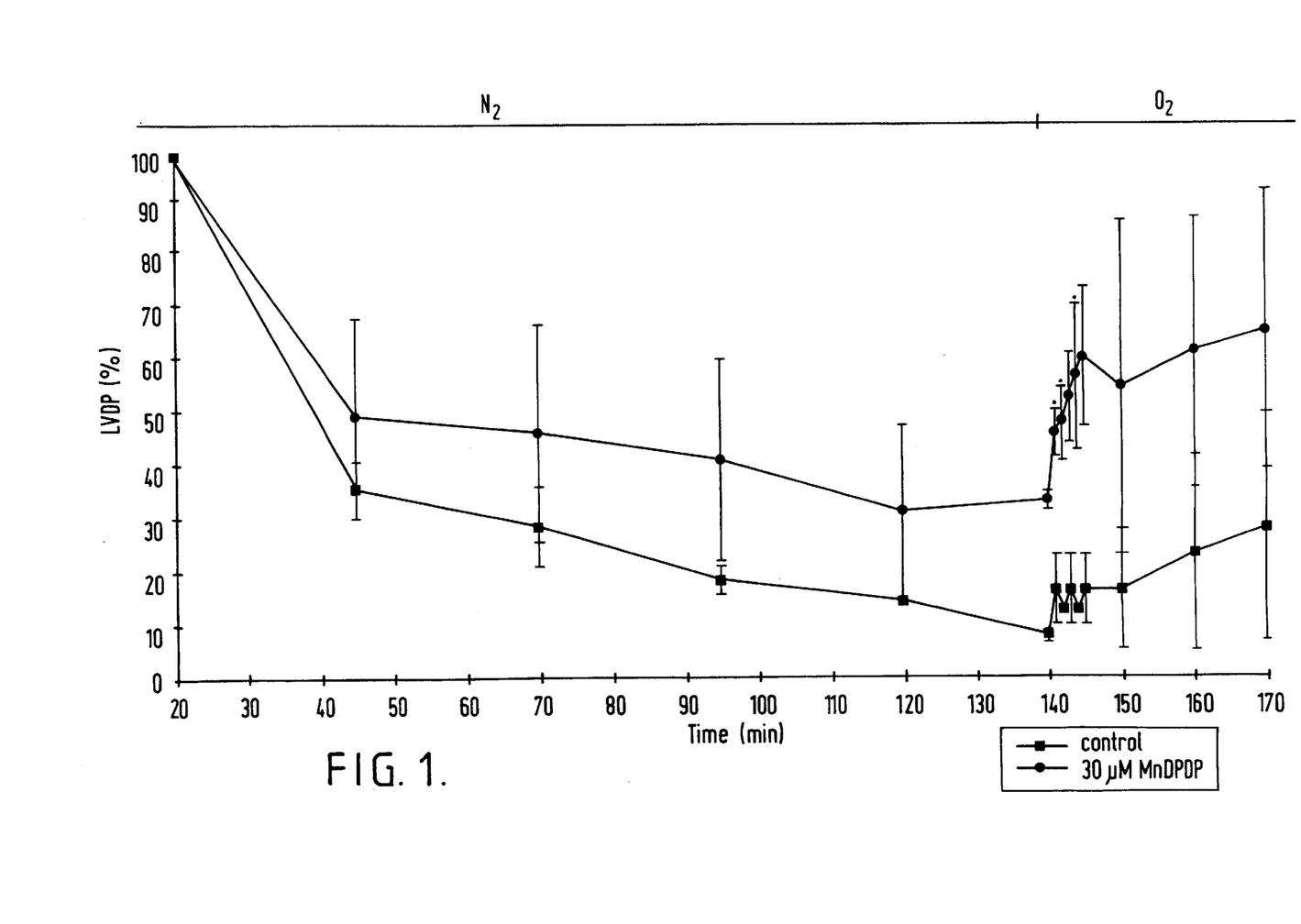
FIG. 1 illustrates changes in left ventricular developed pressure (LVDP) in rat hearts during hypoxia and reoxygenation in the presence of MnDPDP (30 $\mu$M). LVDP is expressed as a percentage of values obtained in the control period. Mean values ±SD are shown. * indicates significant differences between the two groups (p<0.05).

FIG. 1 shows that LVDP, expressed as a percentage of values obtained in the control period, was from 15 to 40% higher with MnDPDP 30 $\mu$M present during hypoxia and reoxygenation. Intergroup differences were significant at the end of hypoxia and during the first 5 minutes of reoxygenation.

Figure 2:
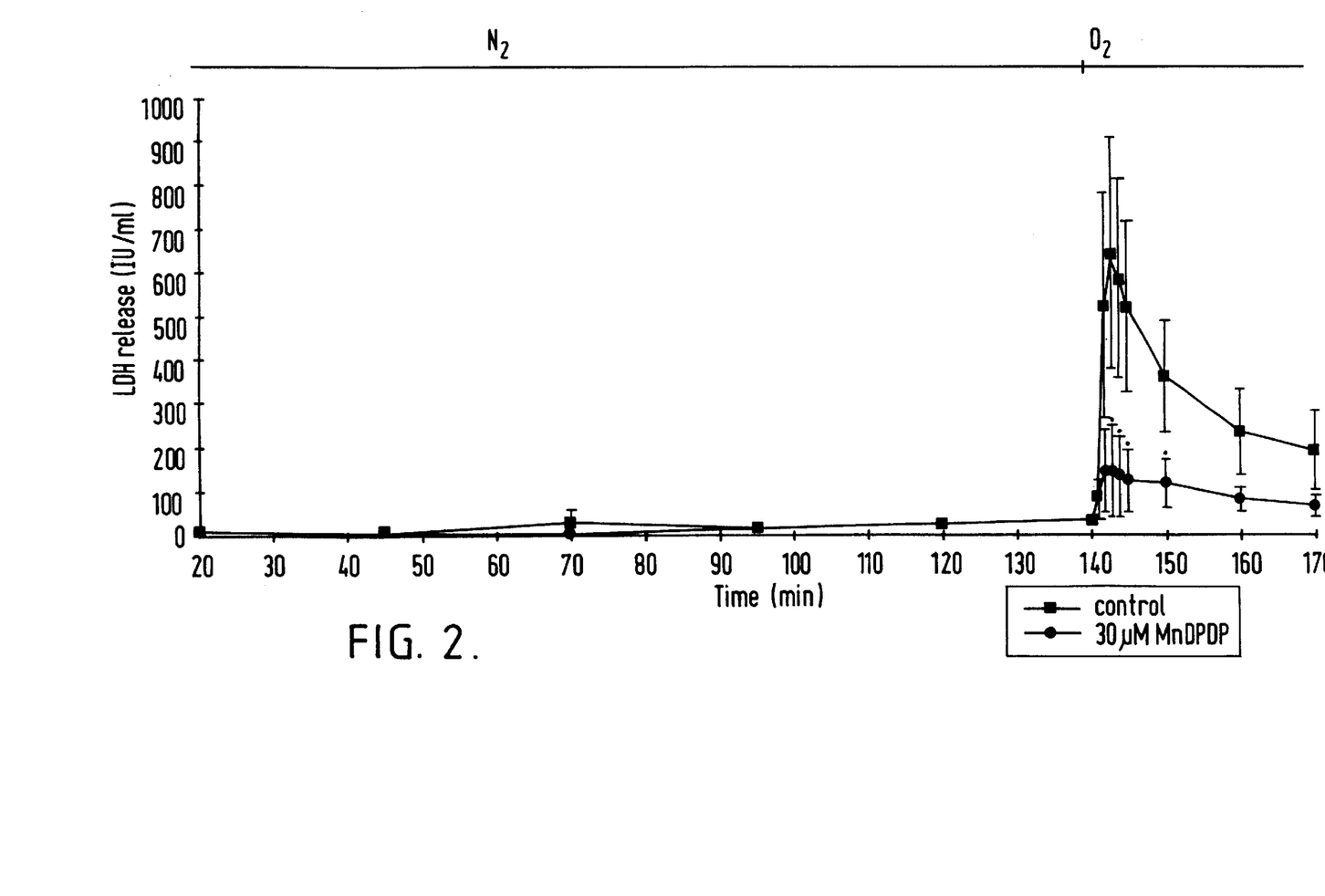
FIG. 2 illustrates myocardial release of lactate dehydrogenase (LDH) in rat hearts during hypoxia and reoxygenation in the presence of MnDPDP (30 $\mu$M). LDH release is expressed in IU/ml. Mean values ±SD are shown. * indicates significant differences between the two groups (p<0.05).

FIG. 2 shows that MnDPDP greatly reduced myocardial LDH release on reoxygenation. Maximal release (mean values ±SD) after reintroduction of $O_2$ was 654±268 IU/min (third min) and 148±108 IU/min (second min) in the control and MnDPDP groups, respectively. Also the accumulated LDH release showed similar significant differences: 9505±3562 IU/30 min in control hearts, and 2887±1461 IU/min in MnDPDP treated hearts.

Improved contractile function during hypoxia and reoxygenation, and reduced enzyme leakage on reoxygenation is evidence of myocardial protection by MnDPDP 30 μM during hypoxia plus reoxygenation.

EXAMPLE 2

Method:

Pigs were anaesthetized with sodium pentobarbitone 35 mg/kg intravenously (i.v.). After intubation a respirator was used to ventilate the animals with room air, if necessary supplemented with $O_2$ up to a total of 30%. Anaesthesia was maintained by continuous infusion of 0.5–5 mg/kg/hr Nembutal.

Thoracotomy was performed to expose the heart and the animals were catheterized for various haemodynamic measurements. A catheter was also placed in the jugular vein for substance administration. Blood samples were taken at intervals during preparation for blood gas measurements ($O_2$, $CO_2$).

After at least 30 minutes equilibration the pigs received 1.5 mg/kg i.v. lidocaine to reduce occlusion-induced arrhythmias. 10 minutes later the animals received 10 μmol/kg MNDPDP or a corresponding volume of 0.9% NaCl (1 ml/kg). Thirty minutes later the left anterior descending branch of the left coronary artery (LAD) was occluded by two atraumatic vascular clamps.

Forty minutes later the LAD was reperfused by removal of the clamps. After another 120 minutes, the heart was removed, the coronary artery reoccluded, and the heart perfused with fluorescent microspheres to demonstrate the area at risk, i.e. the nonperfused area during occlusion. The ventricles were sliced into 8–9 slices. After tetrazolium staining the infarct size was measured and expressed as a percentage of area at risk.

Figure 3:
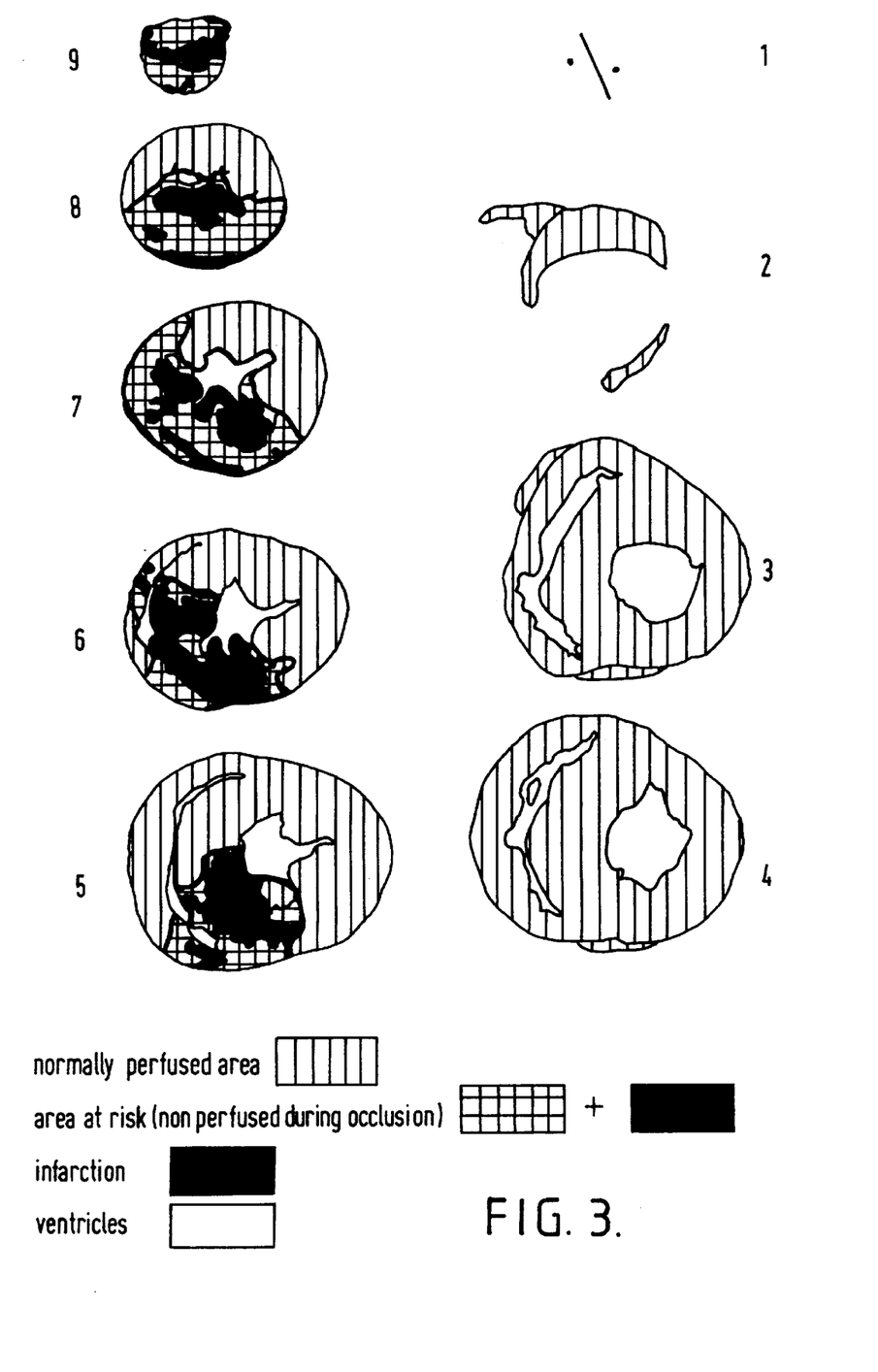
FIG. 3 shows the degree of infarction in pig hearts following treatment with NaCl.
Figure 4:
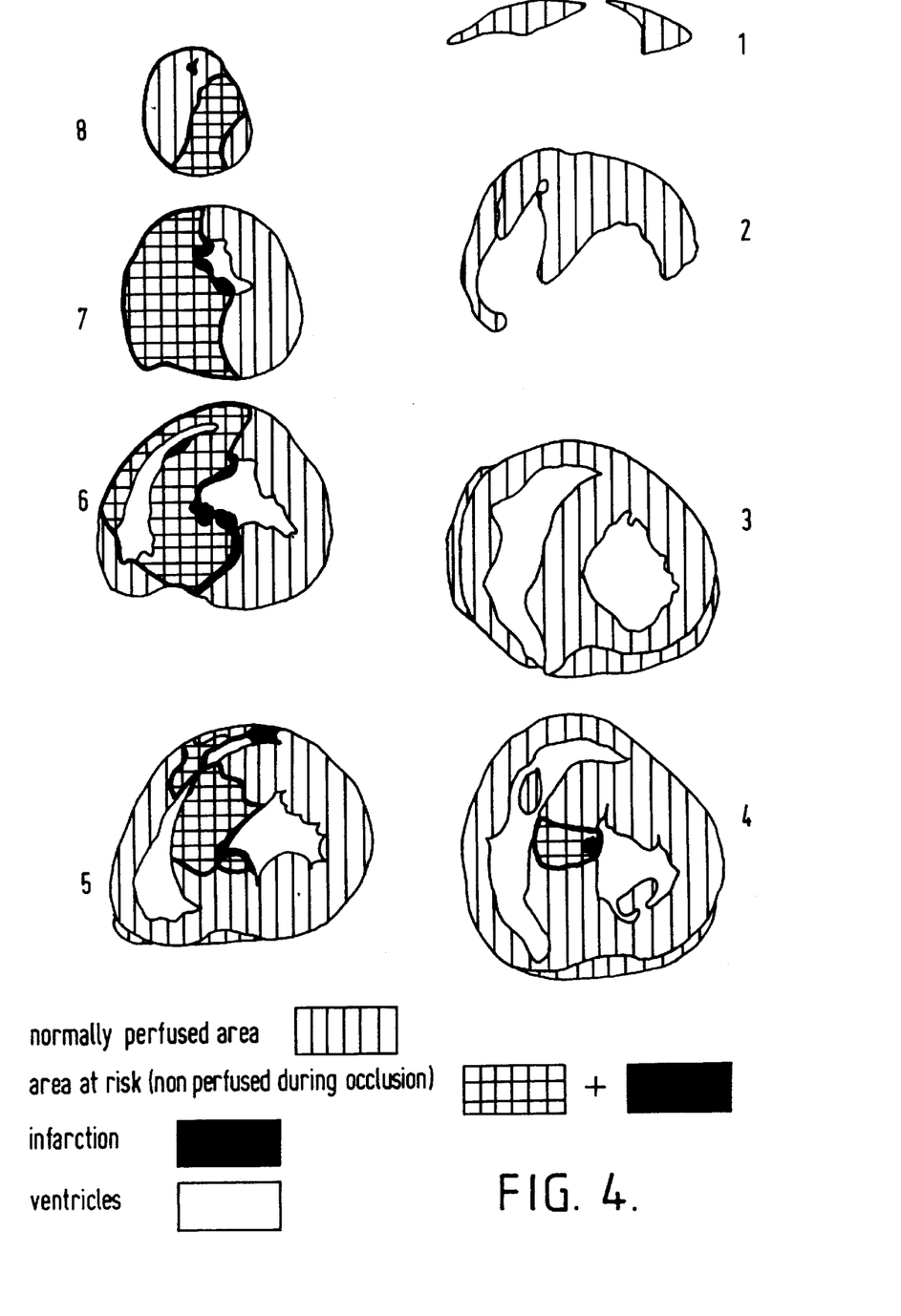
FIG. 4 shows the degree of infarction in pig hearts following treatment with MnDPDP.

Results:

Typical results are shown in FIGS. 3 and 4 attached hereto.

It can be seen that infarct size was larger in the 0.9% NaCl-treated animal (ca. 45% of area at risk) (FIG. 3) than in the MnDPDP-treated animal (ca. 6% of area at risk) (FIG. 4).

It is clear from FIGS. 3 and 4 that the manganese compound MNDPDP (mangafodipir), when injected into the animal before occlusion of LAD, unexpectedly protects the heart muscle from deleterious effects of occlusion-reperfusion.

What is claimed is:

1. A method of treatment of the human or non-human animal body to combat or prevent conditions associated with the presence of free radicals in the body, said method comprising administering to said body a compound of formula I or a metal chelate or salt thereof wherein in formula I
each $R^1$ independently represents hydrogen or —$CH_2COR^5$;
$R^5$ represents hydroxy, optionally hydroxylated alkoxy, amino or alkylamido;
each $R^2$ independently represents a group $XYR^6$;
X represents a bond, or a $C_{1-3}$ alkylene or oxoalkylene group optionally substituted by a group $R^7$;
Y represents a bond, an oxygen atom or a group $NR^6$;
$R^6$ is a hydrogen atom, a group $COOR^8$, an alkyl, alkenyl, cycloalkyl, aryl or aralkyl group optionally substituted by one or more groups selected from $COOR^8$, $CONR^8_2$, $NR^8_2$, $OR^8$, =$NR^8$, =O, $OP(O)(OR^8)R^7$ and $OSO_3M$;
$R^7$ is hydroxy, an optionally hydroxylated, optionally alkoxylated alkyl or aminoalkyl group;
$R^8$ is a hydrogen atom or an optionally hydroxylated, optionally alkoxylated alkyl group;
M is a hydrogen atom or one equivalent of a physiologically tolerable cation;
$R^3$ represents a $C_{1-8}$ alkylene group, a 1,2-cycloalkylene group, or a 1,2-arylene group; and
each $R^4$ independently represents hydrogen or $C_{1-3}$ alkyl.

2. A method as claimed in claim 1 wherein in formula I:
$R^5$ is hydroxy, $C_{1-8}$ alkoxy, ethylene glycol, glycerol, amino or $C_{1-8}$ alkylamido;
X is a bond or a group selected from $CH_2$, $(CH_2)_2$, CO, $CH_2CO$, $CH_2CH_2CO$ or $CH_2COCH_2$;
Y is a bond;
$R^6$ is a mono- or poly(hydroxy or alkoxylated) alkyl group or a group of the formula $OP(O)(OR^8)R^7$; and
$R^7$ is hydroxy, or an unsubstituted alkyl or aminoalkyl group.

3. A method as claimed in claim 1 wherein in formula I, $R^3$ is ethylene and each group $R^1$ represents —$CH_2COR^5$ in which $R^5$ is hydroxy.

4. A method as claimed in claim 1 in which the compound of formula I is N,N'-bis-(pyridoxal-5-phosphate)-ethylenediamine-N,N'-diacetic acid.

5. A method as claimed in claim 1 wherein said metal chelate comprises a metal ion selected from the alkali and alkaline earth metals and metals having an atomic number of from 22–31, 42, 44 and 58–70.

6. A method as claimed in claim 5 wherein said metal chelate has a $K_a$ in the range of from $10^9$ to $10^{25}$.

7. A method as claimed in claim 5 wherein said metal chelate has a $K_a$ in the range of from $10^{12}$ to $10^{22}$.

8. A method as claimed in claim 5 wherein said metal chelate has a Ka value smaller by a factor of at least $10^3$ than the $K_a$ value of the corresponding iron ($Fe^{3+}$) chelate.

9. A method as claimed in claim 5 wherein said metal ion is selected from $Na^+$, $Mn^{2+}$, $Ca^{2+}$, $Cu^+$, $Cu^{2+}$, $Mg^{2+}$, $Gd^{3+}$ and $Zn^{2+}$.

10. A method as claimed in claim 1 wherein said compound is the manganese (II) chelate of N,N'-bis-(pyridoxal-5-phosphate)-ethylenediamine-N,N'-diacetic acid.

11. A method as claimed in claim 1 wherein said condition is a reperfusion-induced injury.

12. A method as claimed in claim 1 herein said injury is a result of myocardial reperfusion.

13. A method as claimed in claim 1 wherein said injury is associated with a thrombolytic treatment, a cardiopulmonary bypass, percutaneous transluminal coronary angioplasty, or is a result of cardiac or transplantation surgery.

14. A method as claimed in claim 1 wherein said condition is a radiation-induced injury.

15. A method as claimed in claim 1 wherein said compound of formula I or a metal chelate or salt thereof is administered together with a thrombolytic agent.

16. A pharmaceutical composition comprising a compound of formula I or a metal chelate or salt thereof as defined in claim 1 together with a thrombolytic agent and at least one pharmaceutically acceptable carrier or excipient.

17. A pack containing a compound of formula I or a metal chelate or salt thereof as defined in claim 1 and separately a thrombolytic agent for simultaneous, separate or sequential use during a thrombolytic procedure.

* * * * *